(12) United States Patent
Schaeppi et al.

(10) Patent No.: US 11,978,564 B2
(45) Date of Patent: *May 7, 2024

(54) SYSTEMS AND METHODS TO FACILITATE ADJUSTING CONTENT TO FACILITATE THERAPEUTIC OUTCOMES OF SUBJECTS

(71) Applicant: Solsten, Inc., Edina, MN (US)

(72) Inventors: Joseph Jack Schaeppi, Maple Grove, MN (US); Jonna Maarit Koivisto, Berlin (DE); Zachary Robert Mayne, Bountiful, UT (US)

(73) Assignee: Solsten, Inc., Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/301,853

(22) Filed: Apr. 17, 2023

(65) Prior Publication Data

US 2023/0253126 A1 Aug. 10, 2023

Related U.S. Application Data

(63) Continuation of application No. 17/326,306, filed on May 20, 2021, now Pat. No. 11,646,122.

(51) Int. Cl.
*G16H 80/00* (2018.01)
*G16H 20/30* (2018.01)
(Continued)

(52) U.S. Cl.
CPC ............. *G16H 80/00* (2018.01); *G16H 20/30* (2018.01); *G16H 20/70* (2018.01); *G16H 50/20* (2018.01)

(58) Field of Classification Search
CPC ........ G16H 80/00; G16H 20/30; G16H 50/20; G16H 20/70
(Continued)

(56) References Cited

U.S. PATENT DOCUMENTS 6,904,408 B1 6/2005 McCarthy
7,526,426 B2 4/2009 Shaw
(Continued)

OTHER PUBLICATIONS

PCT Search Report and Written Opinion; PCT Application No. PCT/US2022/013378, dated Feb. 16, 2022 (16 pages).

*Primary Examiner* — Zhen Y Wu
(74) *Attorney, Agent, or Firm* — Esplin & Associates, PC

(57) ABSTRACT

Systems and methods to facilitate adjusting content to facilitate therapeutic outcomes of subjects are disclosed. Exemplary implementations may: obtain subject information related to subject, the subject information characterizing (i) physiological health of the subject, (ii) a psychological profile of the subject defined by parameter values of psychological parameters, and (iii) a therapeutic outcome for the subject to achieve; effectuate, via a client computing platform associated with a caregiver of the subject, presentation of a caregiver interface that presents the subject information and enables the caregiver to provide caregiver input, wherein the caregiver input causes adjustments to (i) content presented to the subject within a game and (ii) an engagement level of the content, wherein the content facilitates achievement of the therapeutic outcome by the subject; and effectuate, based on the caregiver input, presentation of the adjustments to the content via a client computing platform associated with the subject.

18 Claims, 3 Drawing Sheets

(51) Int. Cl.
*G16H 20/70* (2018.01)
*G16H 50/20* (2018.01)

(58) Field of Classification Search
USPC .................................................... 340/573.1
See application file for complete search history.

(56) References Cited

U.S. PATENT DOCUMENTS

| | | |
|---|---|---|
| 8,327,395 B2 | 12/2012 | Lee |
| 8,464,288 B2 | 6/2013 | Pradeep |
| 8,589,328 B1 | 11/2013 | Sharma |
| 8,635,105 B2 | 1/2014 | Pradeep |
| 8,640,021 B2 | 1/2014 | Perez |
| 8,666,835 B2 | 3/2014 | Minnis |
| 8,762,202 B2 | 6/2014 | Pradeep |
| 9,451,303 B2 | 9/2016 | Kothuri |
| 9,569,986 B2 | 2/2017 | Levine |
| 9,936,250 B2 | 4/2018 | Marci |
| 10,007,645 B2 | 6/2018 | Mhatre |
| 10,027,598 B2 | 7/2018 | Seaward |
| 10,229,036 B2 | 3/2019 | Braband |
| 10,499,191 B1 | 12/2019 | Strand |
| 10,638,256 B1 | 4/2020 | Suiter |
| 10,642,848 B2 | 5/2020 | Oros |
| 11,257,583 B2 * | 2/2022 | Chancellor ............ G16H 80/00 |
| 11,392,854 B2 * | 7/2022 | Neumann .............. G06N 20/00 |
| 2005/0288954 A1 | 12/2005 | McCarthy |
| 2006/0105301 A1 * | 5/2006 | Chriss ................. G09B 21/006 340/286.07 |
| 2008/0055071 A1 * | 3/2008 | Chriss ................... G16H 80/00 340/539.12 |
| 2011/0179116 A1 * | 7/2011 | Solomon ................ G06Q 30/02 709/204 |
| 2011/0295687 A1 | 12/2011 | Bilenko |
| 2012/0002848 A1 | 1/2012 | Hill |
| 2012/0036449 A1 | 2/2012 | Minnis |
| 2012/0059785 A1 | 3/2012 | Pascual Leo |
| 2013/0268394 A1 | 10/2013 | Nikankin |
| 2014/0006154 A1 | 1/2014 | Shipman |
| 2014/0128166 A1 * | 5/2014 | Tam ....................... A63F 13/216 463/42 |
| 2014/0317030 A1 | 10/2014 | Shen |
| 2015/0065825 A1 * | 3/2015 | Utley ..................... A24F 47/00 131/270 |
| 2015/0086948 A1 * | 3/2015 | Donadio ................ G16H 10/60 434/236 |
| 2015/0186498 A1 | 7/2015 | Poltorak |
| 2015/0220604 A1 | 8/2015 | Bunnell |
| 2015/0358416 A1 | 12/2015 | Gariepy |
| 2016/0180379 A1 | 6/2016 | Salmon |
| 2016/0219931 A1 * | 8/2016 | Doshi .................... A24F 47/00 |
| 2016/0331279 A1 | 11/2016 | Shpin |
| 2016/0345060 A1 | 11/2016 | Marci |
| 2017/0169191 A1 * | 6/2017 | Bowers ................ A61B 5/4833 |
| 2017/0352083 A1 | 12/2017 | Ruck |
| 2019/0074080 A1 * | 3/2019 | Appelbaum ........... G16H 80/00 |
| 2019/0080055 A1 * | 3/2019 | Bettencourt Da Silva .................. G16H 20/30 |
| 2019/0102802 A1 | 4/2019 | Tuschman |
| 2019/0189261 A1 * | 6/2019 | Kerssens ................ G16H 20/30 |
| 2019/0260703 A1 | 8/2019 | Moskowitz |
| 2019/0261855 A1 * | 8/2019 | Utley .................... A61B 5/7242 |
| 2020/0279633 A1 * | 9/2020 | Sasaki ................... G16H 10/20 |
| 2020/0288979 A1 * | 9/2020 | Utley .................... A61B 5/7242 |
| 2020/0342353 A1 * | 10/2020 | Neumann ............ G06F 9/3838 |
| 2021/0057095 A1 * | 2/2021 | Dunstan ................ G06F 3/167 |
| 2021/0149941 A1 | 5/2021 | Moskowitz |
| 2021/0186410 A1 * | 6/2021 | Nishiyama ............ G16H 50/20 |
| 2021/0202066 A1 * | 7/2021 | Chancellor ............ G16H 80/00 |
| 2021/0295977 A1 * | 9/2021 | Neumann ............. G16H 20/70 |
| 2021/0366591 A1 * | 11/2021 | Khan .................... G16H 40/63 |
| 2022/0139525 A1 * | 5/2022 | Chancellor ............ G16H 10/60 340/531 |
| 2022/0233075 A1 * | 7/2022 | Utley .................... A61B 5/7275 |
| 2022/0238204 A1 | 7/2022 | Schaeppi |
| 2022/0328160 A1 * | 10/2022 | Kosaka ................. G16H 20/30 |
| 2022/0375625 A1 | 11/2022 | Schaeppi |

* cited by examiner

SYSTEMS AND METHODS TO FACILITATE ADJUSTING CONTENT TO FACILITATE THERAPEUTIC OUTCOMES OF SUBJECTS

FIELD OF THE DISCLOSURE

The present disclosure relates to systems and methods to facilitate adjusting content to facilitate therapeutic outcomes of subjects.

BACKGROUND

As use of online platforms and mobile applications increases, individuals may seek counsel for mental health, recovery, and/or other therapeutic outcomes virtually while still being guided by caregivers. Input from the caregivers may facilitate the individuals achieving the therapeutic outcomes via interactions of the individuals with content of online platforms.

SUMMARY

One aspect of the present disclosure relates to a system configured to facilitate adjusting content for a subject through a caregiver interface to facilitate therapeutic outcomes for the subject. The system may obtain subject information that characterizes a psychological profile of the subject, physiological health of the subject, the therapeutic outcomes, and/or other information. A caregiver of the subject may be presented a caregiver interface that presents the subject information and enables the caregiver to cause adjustments to the content presented to the subject via a game, for example, and cause adjustments to an engagement level of the game. Presentation of the adjustments may be effectuated via a client computing platform associated with the subject. The adjustments may facilitate achievement of the therapeutic outcomes by the subject and may gradually disengage the subject from the game upon progress and achievement of the therapeutic outcomes. Thus, the subject may work to achieve the therapeutic outcomes via a game or other digital experience and with input from their caregiver.

One aspect of the present disclosure relates to a system configured to facilitate adjusting content to facilitate therapeutic outcomes of subjects. The system may include one or more hardware processors configured by machine-readable instructions, an outcome interface, and/or other components. Machine-readable instructions may include one or more instruction components. The instruction components may include one or more of obtainment component, interface presentation component, adjusting component, content identifying component, and/or other instruction components.

The obtainment component may be configured to obtain subject information related to a subject. The subject information may characterize (i) physiological health of the subject, (ii) a psychological profile of the subject, and (iii) a therapeutic outcome for the subject to achieve. The psychological profile may be defined by parameter values of psychological parameters.

The interface presentation component may be configured to effectuate presentation of a caregiver interface. Effectuation of presentation the caregiver interface may be via a client computing platform associated with a caregiver of the subject. The caregiver interface may present the subject information and enable the caregiver to provide caregiver input. The caregiver input may cause adjustments to (i) content presented to the subject within a game, (ii) an engagement level of the content, and/or other information. The content may facilitate achievement of the therapeutic outcome by the subject.

The adjusting component may be configured to effectuate presentation of the adjustments to the content via client computing platform associated with the subject. The effectuation of presentation may be based on the caregiver input.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
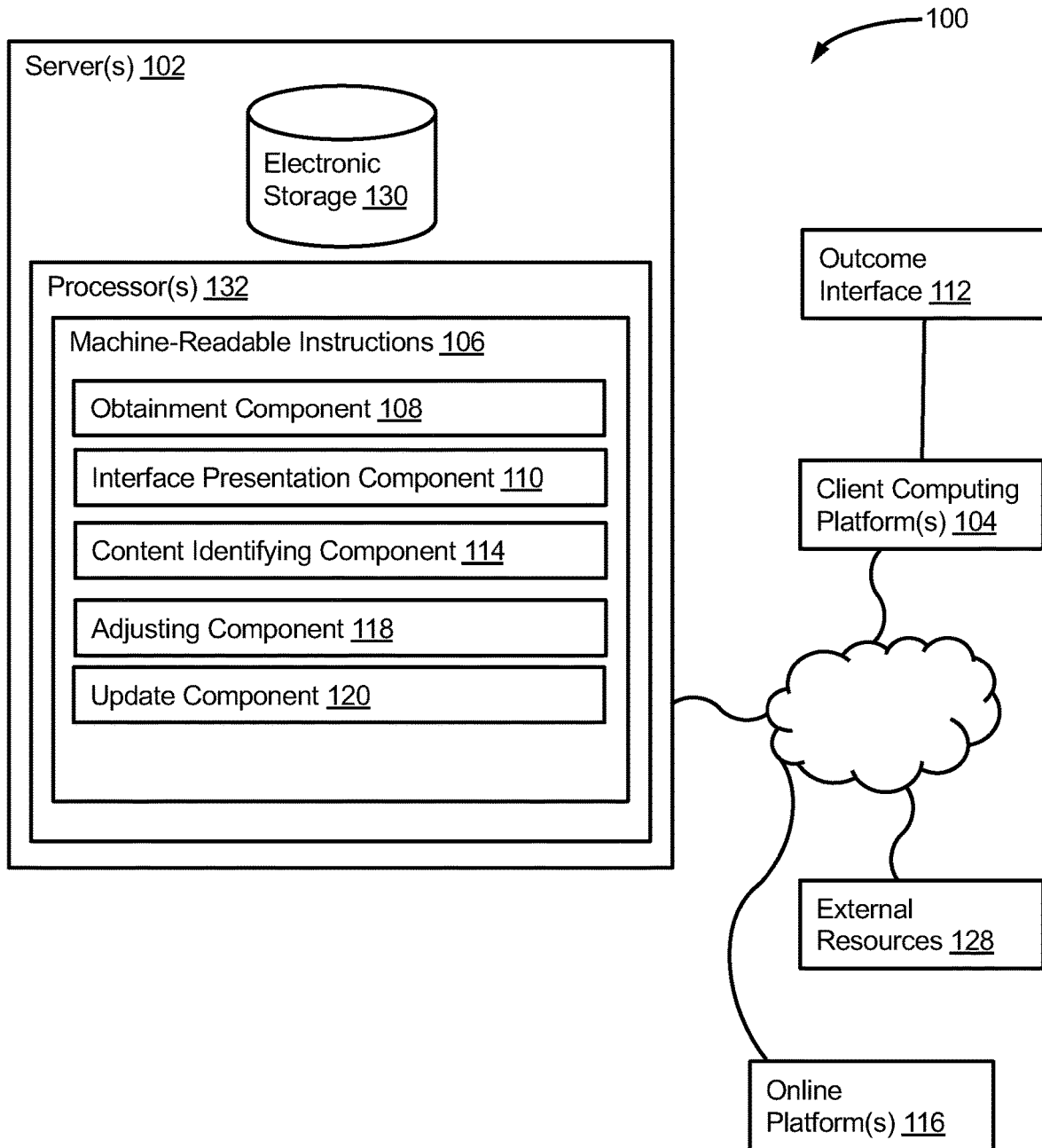
FIG. 1 illustrates a system configured to facilitate adjusting content to facilitate therapeutic outcomes of subjects, in accordance with one or more implementations.

FIG. 1 illustrates a system 100 configured to facilitate adjusting content to facilitate therapeutic outcomes of subjects, in accordance with one or more implementations. The content may be presented to the subjects via online platforms. As used herein, "online platform" or variations thereof may include or provide a digital experience. A digital experience may include one or more of a game (e.g., online via web browser, via desktop application, via mobile application, via game console, etc.), a website (e.g., retailers), a mobile application, a desktop application, a social network platform, a service provider (e.g., E-mail provider), and/or other digital experiences. Such digital experiences may collect similar information related to its subjects and provide some of the same interactions or similar interactions between individual subjects, between the individual subjects and virtual content, and/or other interactions. Virtual content (or pieces thereof) may include one or more of game content, social media content, publicity content, and/or other virtual content. The game content may include one or more of a player-controlled character, a non-player-controlled character, a task, a quest, an assignment, a mission, a level, a chapter, a mini-game, a virtual item, a virtual resource (e.g., weapon, tool), an in-game power, an in-game skill, an in-game technology, and/or other pieces of game content. By way of non-limiting example, virtual items may include one or more of clothing, pets, transportation units (e.g., aircrafts, motor vehicles, watercrafts, etc.), units, buildings, and/or other virtual items. The social media content and the publicity content may include one or more of an image, a video, a description, a financial component (e.g., for purchasing, selling, trading, donating, etc.), and/or other content. Online platforms 116 may be accessed by the subjects via client computing platform(s) 104.

In some implementations, system 100 may include one or more servers 102, a caregiver interface 112, online platforms 116, and/or other components. Server(s) 102 may be configured to communicate with one or more client computing platforms 104 according to a client/server architecture and/ or other architectures. Client computing platform(s) 104 may be configured to communicate with other client computing platforms via server(s) 102 and/or according to a peer-to-peer architecture and/or other architectures. Subjects may access system 100 via client computing platform(s) 104.

Server(s) 102 may be configured by machine-readable instructions 106. Machine-readable instructions 106 may include one or more instruction components. The instruction components may include computer program components. The instruction components may include one or more of obtainment component 108, interface presentation component 110, content identifying component 114, adjusting component 118, update component 120, and/or other instruction components.

Obtainment component 108 may be configured to obtain subject information related to individual subjects. The subject information may characterize (i) physiological health of a subject, (ii) a psychological profile of the subject, (iii) a therapeutic outcome for the subject to achieve, and/or other information related to the individual subjects.

In some implementations, the subject information may include identifying information. By way of non-limiting example, the identifying information may include a username, a gender, an age, a subject name, an email address, a phone number, and/or other identifying information. In some implementations, the identifying information may be associated with the psychological profile to identify the subject. In some implementations, the psychological profile may include the identifying information to identify the subject.

The physiological health of the subject may be characterized by subject health information. The subject health information may include values for one or more of cardiovascular parameters, sleep parameters, activity parameters, diet parameters, and/or other parameters. The subject health information (i.e., parameter included thereof) may specify measurable, recordable, and/or determined information. The values corresponding to the parameters included in the subject health information may be a particular value, numerical or non-numerical, that characterizes the subject.

By way of non-limiting example, the cardiovascular parameters may include a heart rate, a resting heart rate of the subject, a respiratory rate of the subject, blood pressure of the subject, oxygen saturation of the subject, heart variability, heartbeat strength, heartbeat rhythm, and/or other cardiovascular parameters. By way of non-limiting example, the sleep parameters may include hours of sleep, sleep quality, motion during sleep, breathing patterns during sleep, and/or other sleep parameters. By way of non-limiting example, the activity parameters may include minutes exercised; distance walked, ran, cycled, and/or swam; speed of the walk, the run, the cycle, and the swim; inclination of the walk, the run, and the cycled; acceleration, time standing, and/or other activity parameters. By way of non-limiting example, diet parameters may include caloric intake, weight, weight goal, height, body mass index (BMI), various vitamin intake, food restrictions, food intake, liquid intake, substance intake, and/or other diet parameters. Some or all of the subject health information may be measured, recorded, or otherwise determined at a medical office, remotely by the subject (e.g., at home), and/or other location. It is to be expressly understood, however, that the subject health information obtained are for the purpose of illustration and description only and are not intended as a definition of the limits of this disclosure. By way of non-limiting illustration, first subject health information may characterize the physiological health of a first subject.

The psychological profile may be defined by parameter values of psychological parameters. The parameter values of the psychological parameters may characterize mental health and/or other information (e.g., medical history, past adversities, etc.) of the subject. By way of non-limiting illustration, a first psychological profile may characterize the mental health and/or other information of the first subject.

The parameter values may define, by way of non-limiting example, achievement motivation, motivation, personality inventory, cultural values, competitiveness, positive and negative affect before, during, and/or after engagement with the online game (i.e., emotions), communication style, personal values, daily routines/activities, life/gaming pain points, life/gaming hopes and aspirations, wellbeing, subject experience, gaming/experience using time, subscription behavior, affinity information, personality, emotional style, goal orientation, goal commitment, ego and task orientation, relatedness, sense of community, social influence, social identity, group identification, we-identity, quality of life, satisfaction with life, work-related quality of life, mindfulness, happiness, emotional intelligence, self-awareness/internal awareness, external awareness, connectedness to nature, social connectedness, social bonding, perceived stress, depression, anxiety, decision-making style, thinking style, critical thinking, cognitive approach to learning, learning style, attributional style, internality-externality, stability-instability, global-specific, creativity, curiosity, playfulness, exploration, mental strength, grit, flourishing, gratitude, inspiration, spirituality, hedonism, materialism/material values, perceptions, sentiments, and/or other psychological parameters.

Achievement motivation may include compensatory effort, competitiveness, confidence in success, dominance, eagerness to learn, engagement, fearlessness, flexibility, flow, goal setting, independence, internality, persistence, preference in difficult tasks, pride in productivity, self-control, status orientation, ambition, self-assurance, and/or other psychological parameters. Motivation may include mastery, purpose, autonomy, and/or other psychological parameters.

Personality inventory may include neuroticism, openness, conscientiousness, extraversion, and agreeableness and/or other psychological parameters. Neuroticism may include anxiety, impulsiveness, vulnerability, and/or other psychological parameters. Openness may include fantasy, feelings/empathy, action, and/or other psychological parameters.

Conscientiousness may include achievement striving, competence, self-discipline, and/or other psychological parameters. Extraversion may include warmth assertiveness, activity, and/or other psychological parameters. Agreeableness may include trust, altruism, modesty, and/or other psychological parameters.

Cultural values may include individualism, indulgence, long term orientation, masculinity, power distance, uncertainty avoidance, and/or other psychological parameters. Competitiveness may include avoidant, collaborative, competitive affectivity, dependent, dominant, general competitiveness, independent, personal enhancement, and/or other psychological parameters.

Positive and negative affect before, during, and/or after engaging in the online game may include hostility, joviality, negative emotions, positive emotions, sadness, self-assurance, and/or other psychological parameters. Communication style may include feeler, intuitor, sensor, thinker, and/or other psychological parameters.

Wellbeing may include social wellbeing, psychological wellbeing, physical wellbeing, physical activity, sleep, bounded reciprocity, resilience grit, and/or other psychological parameters.

Personality may include anger, hostility, depression, self-conscientiousness, excitement-seeking, positive emotions, gregariousness, ideas, values, aesthetics, tender-mindedness, straightforwardness, compliance, deliberation, order, dutifulness, and/or other psychological parameters.

Emotional style may include resilience, outlook, social intuition, self-awareness, sensitivity to context, attention, and/or other psychological parameters.

Goal orientation may include mastery approach/learning goal orientation, performance approach/performance goal orientation, performance avoid/avoidance goal orientation, and/or other psychological parameters.

Work-related quality of life may include structure, boundaries, focus, efficiency, information provision, communication, psychological support, stress at/from work, psychological safety, connectedness with team, motivation to work, adaptability, job/career satisfaction, control at work, homework interface, general wellbeing, working conditions, and/or other psychological parameters.

Mindfulness may include observing, describing, acting with awareness, non-judgment, non-reactivity, and/or other psychological parameters.

Emotional intelligence may include emotion perception, emotion expression, emotion management, emotion regulation, impulse control, relationships, stress management, and/or other psychological parameters.

Social connectedness may include social connectedness, loneliness, membership self-esteem, private self-esteem, public self-esteem identity self-esteem, interdependent self, independent self, social avoidance, social distress, and/or other psychological parameters.

Decision-making style may include respected, confident, spontaneous, dependent, vigilant, avoidant, brooding, intuitive, anxious, and/or other psychological parameters.

Thinking style may include intuitive, experiential, analytical, rational, and/or other psychological parameters.

Cognitive approaches to learning may include avoidant, participative, competitive, collaborative, dependent, independent, and/or other psychological parameters.

Learning style may include visual (spatial), aural (auditory-musical), verbal (linguistic), physical (kinesthetic), logical (mathematical), social (interpersonal), solitary (intrapersonal), and/or other psychological parameters.

Mental strength may include tenacity, confidence, optimism, adaptability, self-awareness, reliability, responsibility, well-being, and/or other psychological parameters.

Flourishing may include positive emotion, engagement, relationships, meaning, accomplishment, health, loneliness, and/or other psychological parameters.

The parameter values of the psychological parameters may be a number score on a predetermined range unique to each psychological parameter, a letter score, and/or other type of value than may characterize intensity of the psychological parameter that the parameter value defines and thus a particular subject as whole. The intensity may represent significance of a given psychological parameter that the particular subject is.

A given therapeutic outcome may include multiple elements for improvement. By way of non-limiting example, elements for improvement may include one or more of an addiction, an injury, an illness, a disability, and/or other element for improvement. For example, an injury may include recovery from a surgery, rehabilitation, and/or other injury. For example, an illness may include a chronic disease, a recoverable disease, a terminal disease, a mental illness, and/or other illness. For example, a disability may include a physical disability, a learning disability, and/or other disability.

A given therapeutic outcome may be associated with changes in parameter value for one or a plurality of the psychological parameters, the cardiovascular parameters, the sleep parameters, the activity parameters, the diet parameters, and/or other parameters that correspond to the given therapeutic outcome. As such, the given therapeutic outcome may be achieved by achieving the associated changes in parameter value for the corresponding one or more psychological parameters and/or subject health information. In some implementations, obtainment component 108 may be configured to obtain (e.g., from electronic storage 130, cloud storage, external resources 128) the psychological parameters, the cardiovascular parameters, the sleep parameters, the activity parameters, the diet parameters, and/or other parameters that correspond to and/or facilitate achievement of particular therapeutic outcomes obtained. Individual ones of the elements for improvement may be associated with changes in parameter value for one or more of the psychological parameters, the cardiovascular parameters, the sleep parameters, the activity parameters, the diet parameters, and/or other parameters. By way of non-limiting illustration, the subject information may include a first therapeutic outcome for the first subject. The first therapeutic outcome may include a first element (e.g., depression) and a second element (e.g., sobriety). The first therapeutic outcome may be associated with changes in parameter value for a first psychological parameter (e.g., flexibility with regards to achievement motivation) and a first activity parameter (e.g., minutes exercised).

Changes in the parameter value for one or more of the psychological parameters, the cardiovascular parameters, the sleep parameters, the activity parameters, the diet parameters, and/or other parameters may include a change in percentage or a particular amount of points, score, or other type of value in each of the parameter values that the therapeutic outcome corresponds to (e.g., the parameter value for each of the first psychological parameter and the first activity parameter increase by 10%); a collective change in percentage or a collective change in a particular amount of points, score, or other type of value in the parameter values that the therapeutic outcome corresponds to (e.g., the parameter values for the first psychological parameter and the first activity parameter increase by 30 points collectively); a change in percentage or a particular amount of point, score, or other type of value within a particular amount of time (i.e., a particular rate of change); the parameter value (e.g., a psychological parameter, a diet parameter, etc.) reaching a particular threshold; the parameter value reaching the particular threshold at a particular time or within a particular amount of time; and/or other changes in the parameter value for the one or more psychological parameters and/or subject health information. The change in the percentage or particular amount of points, score, or other type of value may include an increase or decrease of such. The particular threshold may be predetermined and correspond with a given parameter associated with the given therapeutic outcome and/or modifiable by caregivers. It should be understood that the changes parameter values to the various parameters associated with the therapeutic outcome described herein are not intended to be limiting and parameter values to the various parameters may change in a plurality of ways not explicitly listed herein.

Interface presentation component 110 may be configured to effectuate presentation of caregiver interface 112 that presents the subject information and/or other information and enables the caregiver to provide caregiver input. Caregiver interface 112 may be presented within or outside online platforms 116. Caregiver interface 112 may be presented via a client computing platform 104 associated with the caregiver of the subject. Caregivers of subjects may include one or more of a doctor, a therapist, a psychiatrist, a mentor, a specialist (e.g., addiction specialist), a family member, a friend, and/or other caregivers. Caregiver interface 112 may include one or more user interface elements. The user interface elements may be configured to facilitate entry and/or selection of caregiver input. By way of non-limiting illustration, the user interface elements may include one or more of text input fields, drop down menus, check boxes, virtual buttons, virtual dials, virtual sliders, and/or other user interface elements. The caregiver input may cause adjustments to content presented to the subject within the game or digital experience, adjustments to an engagement level of the content, and/or include other information presented to the subject. The content may facilitate achievement of the therapeutic outcome by the subject.

The content presented to the subject may include one or more of a recommendation for the subject, status display and composition, a difficulty level, rewards, an interaction interface, and/or other content. The recommendations may include one or more of a to-do list, a quest, educational information, an alliance, a website, a mini-game, and/or other recommendations for the subject within, e.g., a game, hosted by online platform 116. The status display and composition may include a metric of achievement, a leaderboard, aesthetics, and/or other status displays and compositions presented within the game. The metric of achievement may include one or more hours spent on online platform 116, hours spent interacting with the game, hours spent communicating with the caregiver, an amount of milestones met, an amount of rewards held by the subject, and/or other metrics of achievement. The leaderboard may present the metric of achievement by the subject amongst other subjects. The leaderboard may be or appear to be viewable by the other subjects (e.g., given that the subject is status oriented). For example, aesthetics may include one or more of a color, a font, an undertone of messages included in the content (e.g., calming, soothing, direct/frank, etc.), and/or other aesthetics. The rewards may include badges, streaks, points, virtual items, virtual characters, and/or other rewards presented/provided to the subject within the game. The interaction interface may enable the subject to interact with other subjects that have the same or a similar therapeutic outcome, the caregiver or other caregivers, an automated help bot, and/or other individuals.

Adjustments to the engagement level may gradually adjust the content between a plurality of engagement levels and/or other levels. In some implementations, adjusting the content may include adjusting particular ones of the content presented to the subject. In some implementations, adjusting the content may include adjusting the content itself and features thereof. For example, adjusting the content that is presented may include ceasing presenting the subject on a leaderboard for a particular achievement amongst other subjects and providing/presenting the rewards to the subject. Such adjustment may be based on the subject information and/or the caregiver input indicating that the subject is motivated by rewards more than status. As another example, adjusting the content itself or features thereof may include adjusting a leaderboard presented to include blue hues. As another example, adjusting the content that is presented may include ceasing presentation of the leaderboard and presenting daily to-do lists for the subject to complete based on the subject information indicating that the subject is goal oriented. For example, adjusting the content itself or features thereof may include presenting an animation upon completion of an item from the to-do list.

The engagement levels may range between a highly engaging level to a less-engaging routine level. Adjusting the engagement level may adjust an amount of the rewards presented/provided to the subject and when or how often the rewards are presented to the subject. The highly engaging level may be time consuming and compelling, so the subject continuously interacts and engages with the game. The highly engaging level may include more rewards provided to the subject (e.g., 10 stars instead of 3 stars for an achievement) and/or more often (e.g., for small achievements such as replying to a message from a caregiver in addition to winning a mini-game). The less-engaging routine level may be maintainable long-term so that the subject may interact with or maintain interaction with the content over a long period of time (e.g., interacts daily for 30 minutes). The less-engaging routine level may include less rewards provided to the subject and/or less often. The gradual adjustment of the content responsive to adjusting the engagement level may occur over a particular period of time (e.g., one month, one week, 21 days, etc.). The particular period of time may be specified by the caregiver via caregiver interface 112, fixed based on the therapeutic outcome, or fixed based on the subject information. In some implementations, the particular period of time may be determined based on a specified period of time by the caregiver via caregiver interface 112, the therapeutic outcome, the subject, the subject information, and/or other information.

In some implementations, the caregiver input may include milestones to a path to achieve the therapeutic outcome. The path may be a plan to achieve the therapeutic outcome. The path may be defined by the caregiver via caregiver interface 112. The milestones may refer to objectives the subject achieves individually to achieve the therapeutic outcome. An individual milestone may be an element for improvement of the therapeutic outcome. In some implementations, the milestones of the path may be defined for achievement in a particular order. In some implementations, the caregiver input may define which of the milestones have been achieved, how much of individual milestones have been achieved, and/or other information regarding the path to achieve the therapeutic outcome.

In some implementations, the caregiver input may characterize the change in the parameter value to the one or more psychological parameters and/or other parameters (corresponding to the therapeutic outcome). In some implementations, the caregiver input may include notes about and associated with the changes in the parameter value. Thus, adjusting the content (by adjusting component 118) and effectuation thereof may be based on the caregiver input.

In some implementations, the caregiver input provided by the caregiver via the caregiver interface 112 may include timing information. The content may be gradually adjusted in accordance with the timing information. The timing information may define an amount of time for the subject to achieve the therapeutic outcome. For example, the content may be gradually adjusted so that a given therapeutic outcome is achieved within 6 months. In some implementations, the timing information may be predetermined, selected by the subjects, or entered by the subjects. In some implementations, the timing information may be predetermined based on the therapeutic outcome. For example, a therapeutic outcome may include a calmness/decrease anxiety element and a management of anger outbursts element to be achieved in 18 months. In some implementations, the predetermined timing information may be modified based on the caregiver input. In some implementations, the predetermined timing information may have minimum and/or maximum parameters that the timing information may not be modified past. For example, the management of anger outbursts may be achieved in a minimum of 12 months and the calmness/decrease anxiety may be achieved in a minimum of 6 months. Based on the timing information, effectuation of presentation of the adjustments may be affected.

In some implementations, interaction correlations between the content of individual online platforms 116 and particular psychological parameters (defined by psychological profiles) or other parameters may be determined or obtained. The interaction correlations may be determined or obtained as described in co-pending U.S. application Ser. No. 17/157,661 entitled "SYSTEMS AND METHODS TO LINK PSYCHOLOGICAL PARAMETERS ACROSS VARIOUS PLATFORMS", the disclosure of which is incorporated by reference in its entirety herein.

In some implementations, content identifying component 114 may be configured to receive the caregiver input. In some implementations, content identifying component 114 may be configured to identify content for online platform 116 to be presented as the adjustment to the content. The content may be identified based on the caregiver input, the subject information, the therapeutic outcome, the parameters associated with the therapeutic outcome, the interaction correlations, and/or other information. In some implementations, content identifying component 114 may be configured to cause the content to be generated for the online platform 116. In some implementations, the content may be generated based on current content currently presented by the individual online platform 116, content not yet presented by individual online platform 116, other content associated with individual online platform 116, content not associated with individual online platform 116, the caregiver input, the subject information, the therapeutic outcome, the parameters associated with the therapeutic outcome, the interaction correlations, other content, and/or other information.

In some implementations, content identifying component 114 may be configured to transmit the adjustments to online platform 116 for presentation by online platform 116 to the subject in the game (or digital experience). For example, transmission of the identified content may be via the network to online platform 116. The adjustments may be transmitted to the online platforms 116 according to a schedule (e.g., daily at 12 PM), immediately subsequent to identifying the content, upon selection (e.g., by an administrator of system 100) of a virtual button to transmit, and/or at other times or upon other events.

Adjusting component 118 may be configured to effectuate presentation of the adjustments to the content and/or the engagement level via client computing platform 104 associated with the subject. The adjustments may be presented within the game. The adjustments presented may be based on the caregiver input, the subject information, identifications by content identifying component 114, the interaction correlations, and/or the information. The adjustments may further facilitate achievement of the therapeutic outcome. That is, the adjustments presented to the subject may facilitate changes in parameter value to the various parameter(s) that correspond to the therapeutic outcome.

By way of non-limiting illustration, a first adjustment that adjusts the content presented to the first user may be identified based on the caregiver input and presented to the first subject within the game via client computing platform 104 associated with the subject. A second adjustment that adjusts the engagement level to be more engaging may be received via caregiver interface 112 as the caregiver input. Thus, the subject may be presented with more rewards per achievement (e.g., finishing a quest). The first and second adjustment may facilitate changes in the parameter values to the first psychological parameter and the first activity parameter that correspond to the first therapeutic outcome.

In some implementations, obtainment component 108 may be configured to receive interaction information from online platform 116 that host the game or digital experience. The interaction information may characterize engagement by the subjects with the content and/or adjustments thereof. In some implementations, the interaction information may be received in an ongoing manner. The term "ongoing manner", as used herein, may refer to continuing to perform an action (e.g., receive) periodically (e.g., every 30 seconds, every minute, every hour, etc.) until receipt of an indication to terminate. The indication to terminate may include a selection of a virtual button to cease the action, and/or other indications of termination. In some implementations, the indication to terminate may include a predefined time (e.g., a date and time). The predefined time may be defined by an administrator of system 100, the caregiver, the subject, and/or other individuals. In some implementations, individual online platforms 116 may define when the interaction information is received by or sent to obtainment component 108.

The interaction information may define performance of behavior patterns of the individual subjects with or based on the content presented. The performance of the behavior patterns of the individual subjects may include individual actions with the content, sets of actions with the content, ordered sets of actions with the content, time spent by the individual subjects engaging with the content and/or the online platforms, spending patterns of the subjects, completed tasks by the individual subjects, uncompletion tasks by the individual subjects, failure of tasks by the individual subjects, and/or other behavior patterns. In some implementations, the performance of the behavior patterns may include multiple of the individual actions, the sets of actions, and the ordered set of actions. The actions may include one or more of a purchase based on the content, a sale, a trade, a donation, a subject selection of the content, gameplay (e.g., mini-game, battle, competition, etc.) based on the content, communication of the individual subjects with other particular subjects, completion of tasks by the subjects, frequent interaction with the content, formation of alliances by the subjects, collection of items (e.g., hidden virtual jewels), and/or other actions based on or not based on the content. The spending patterns may indicate an amount of currency (e.g., real-world money, virtual money, points, etc.) spent, an amount of currency earned, an amount of currency donated, and/or other indications.

In some implementations, update component 120 may be configured to update the physiological health, the psychological profile, and/or other information of the individual subjects. Updating the physiological health, the psychological profiles (i.e., the parameter values to the psychological parameters), and/or other information may be based on the caregiver input, the interaction information of the individual subjects, and/or other information. For example, the caregiver may input different/updated parameter values for the psychological parameters that are associated with the therapeutic outcome. In some implementations, the physiological health and the psychological profiles may be updated in an ongoing manner. The updates may indicate progress towards achievement of the therapeutic outcome. In some implementations, the psychological profiles of the subjects may include the interaction information. In some implementations, updating the psychological profiles may include updating or recording the interaction information of the subjects. Therefore, the subject information presented to the caregiver via caregiver interface 112 may include the interaction information. The subject health information and the subject information may be stored to electronic storage 130, cloud storage, or other storage by obtainment component 108.

In some implementations, update component 120 may be configured to determine an impact value of the engagement level and/or of the content on the achievement of the therapeutic outcome by the subject. In some implementations, update component 120 may be configured to determine the impact value of the adjustments to engagement level and/or to the content on the achievement of the therapeutic outcome by the subject. Determining the impact value may be based on the subject information, the caregiver input, and/or other information.

In some implementations, the impact value may be determined in an ongoing manner. In some implementations, the impact value may be determined periodically. For example, two weeks after presentation of the adjustments, the impact value may be determined. In some implementations, an individual impact value determined may be associated with a time at which it was determined, particular content or particular adjustments, a particular subject of which the subject information is related to, and/or other information. In some implementations, the impact values and the associated information thereof may be stored as or otherwise included in the subject information of the respective subjects or to electronic storage 130, cloud storage, or other storage upon determination. In some implementations, the impact values may be presented to the caregiver via their client computing platform 104 and/or the subject via their client computing platform 104.

In some implementations, adjusting component 118 may be configured to automatically effectuate presentation of supplementary adjustments to the engagement level and/or the content presented based on machine learning, heuristics, the subject information, the adjustments caused by the caregiver input, and/or other information. The presentation of supplementary adjustments to the engagement level and/or the content presented may be effectuated via client computing platform 104 associated with the subject. The machine learning may include known techniques and novel techniques. The heuristics may include known techniques and novel techniques. In some implementations, adjusting the engagement level based on the machine learning and/or the heuristics may be further based on the impact value. Therefore, as it is determined that the subject is achieving their therapeutic outcome, the engagement level may be adjusting automatically (e.g., to be less time consuming). In some implementations, the adjustments to the content and/or the engagement level may facilitate disengaging the subject from the game. Disengagement from the game may enable the subject to interact with the game in a long-term manner (e.g., to maintain sobriety, to manage post cancer, etc.).

In some implementations, update component 120 may be configured generate a notification of the supplementary adjustments and/or other adjustments to the engagement level and/or the content presented, and/or other notifications. The notification may include how much the engagement level adjusted, what content and features thereof of the game are adjusted (e.g., removed, added, modified), which of the content the subject should focus on, basis for the supplementary adjustments (e.g., changes in the subject information, the interaction information, etc.), and/or information related to the adjustments to the game automatically caused. In some implementations, the notifications may include a caregiver recommendation for the caregiver. In some implementations, the caregiver recommendation may ensure that the subject follows or engages with the supplementary adjustments of the game. In some implementations, the caregiver recommendation may include the supplementary adjustments prior to effectuation thereof so that the caregiver may approve, deny, or modify the supplementary adjustments via caregiver interface 112.

In some implementations, interface presentation component 110 may be configured to effectuate presentation of notifications via the caregiver interface 112 for the caregiver. Subsequent to presentation of the caregiver recommendation via caregiver interface 112 and responsive to the caregiver input to approve, deny, or modify the supplementary adjustments, the supplementary adjustments may be effectuated (i.e., upon approval), not effectuated (i.e., upon denial), or modified based on modifications from the caregiver via caregiver interface 112. In some implementations, interface presentation component 110 may be configured to effectuate presentation of notifications via client computing platform 104 associated with the subject. The notifications for the subject may include what content and features thereof of the game are adjusted (e.g., removed, added, modified), which of the content to focus on, basis for the supplementary adjustments (e.g., "You like to complete lists, here are some curated lists for you"), and/or other information.

Figure 3:
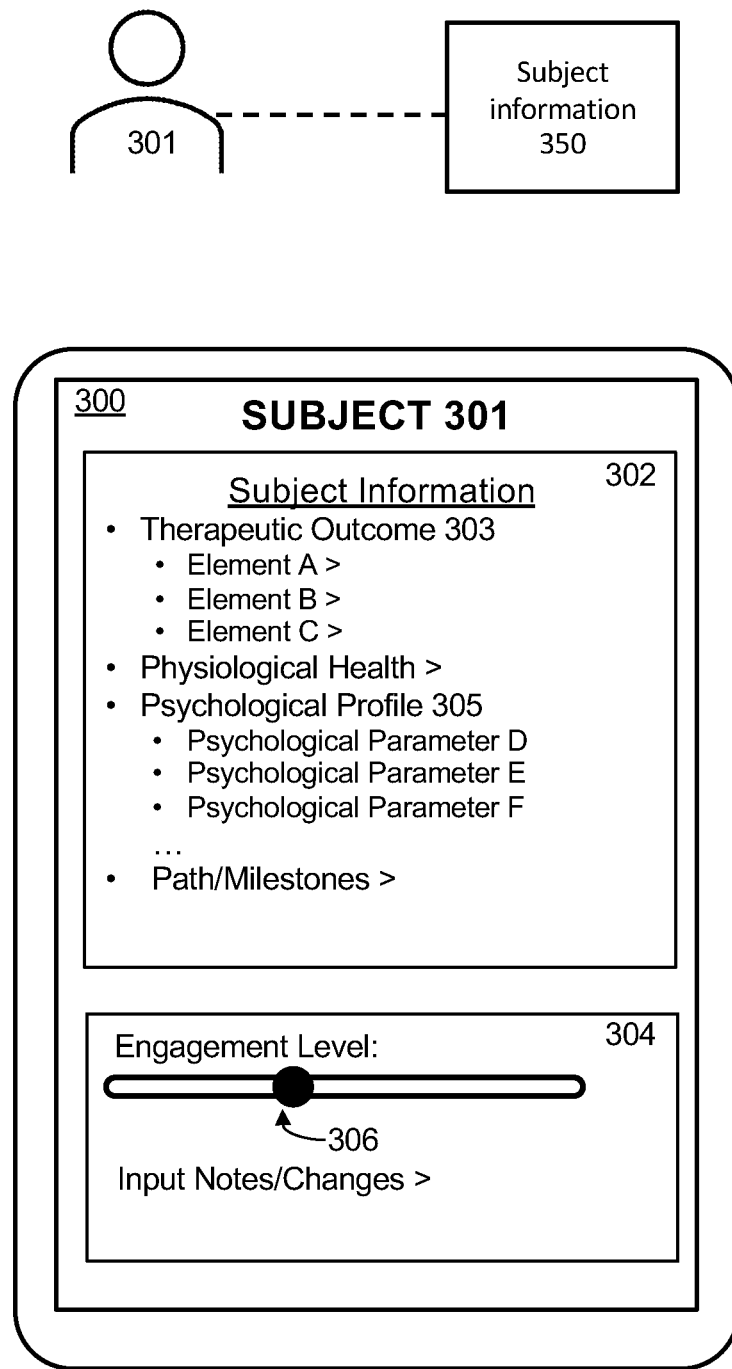
FIG. 3 illustrates an example implementation of the system configured to facilitate adjusting content to facilitate therapeutic outcomes of subjects, in accordance with one or more implementations.

FIG. 3 illustrates an example implementation, in accordance with one or more implementations. FIG. 3 illustrates a subject 301 who is associated with subject information 350. Subject information 350 may be obtained (i.e., by system 100 of FIG. 1) and may include a psychological profile 305, subject health information characterizing physiological health, and a therapeutic outcome 303 for subject 301. Therapeutic outcome 303 (e.g., post illness management) may include elements A, B, and C that subject 301 is to achieve or improve (e.g., post illness anxiety, post illness pain, depression). Psychological profile 305 may define psychological parameters D, E, and F for subject 301 (e.g., indicating motivation by rewards, a to-list, and not status). A caregiver may be presented a caregiver interface 300 that include an information section 302 and an input section 304. Information section 302 may present subject information 350 for subject 301. Input section 304 may enable the caregiver to adjust an engagement level of a game for subject 301 via slider 306, input notes or parameter value changes to various parameters (described in FIG. 1) about subject 301, and/or other information. Based on caregiver input via input section 304, content of the game may be adjusted. For example, to-do lists may be generated and presented within the game for subject 301, rewards may be presented for completion of items on the to-do lists, and status leaderboards may be removed.

In some implementations, server(s) 102, client computing platform(s) 104, and/or external resources 128 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 128 may be operatively linked via some other communication media.

A given client computing platform 104 may include one or more processors configured to execute computer program components. The computer program components may be configured to enable an expert or subject associated with the given client computing platform 104 to interface with system 100 and/or external resources 128, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 128 may include sources of information outside of system 100, external entities participating with system 100, and/or other resources. In some implementations, some or all of the functionality attributed herein to external resources 128 may be provided by resources included in system 100.

Server(s) 102 may include electronic storage 130, one or more processors 132, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 130 may comprise non-transitory storage media that electronically stores information. The electronic storage media of electronic storage 130 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may include one or more virtual storage resources (e.g., cloud storage, a virtual private network, and/or other virtual storage resources). Electronic storage 130 may store software algorithms, information determined by processor(s) 132, information received from server(s) 102, information received from client computing platform(s) 104, and/or other information that enables server(s) 102 to function as described herein.

Processor(s) 132 may be configured to provide information processing capabilities in server(s) 102. As such, processor(s) 132 may include one or more of a digital processor, an analog processor, a digital circuit designed to process information, an analog circuit designed to process information, a state machine, and/or other mechanisms for electronically processing information. Although processor(s) 132 is shown in FIG. 1 as a single entity, this is for illustrative purposes only. In some implementations, processor(s) 132 may include a plurality of processing units. These processing units may be physically located within the same device, or processor(s) 132 may represent processing functionality of a plurality of devices operating in coordination. Processor(s) 132 may be configured to execute components 108, 110, 114, 118, and/or 120, and/or other components. Processor(s) 132 may be configured to execute components 108, 110, 114, 118, and/or 120, and/or other components by software; hardware; firmware; some combination of software, hardware, and/or firmware; and/or other mechanisms for configuring processing capabilities on processor(s) 132. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 114, 118, and/or 120 are illustrated in FIG. 1 as being implemented within a single processing unit, in implementations in which processor(s) 132 includes multiple processing units, one or more of components 108, 110, 114, 118, and/or 120 may be implemented remotely from the other components. The description of the functionality provided by the different components 108, 110, 114, 118, and/or 120 described below is for illustrative purposes, and is not intended to be limiting, as any of components 108, 110, 114, 118, and/or 120 may provide more or less functionality than is described. For example, one or more of components 108, 110, 114, 118, and/or 120 may be eliminated, and some or all of its functionality may be provided by other ones of components 108, 110, 114, 118, and/or 120. As another example, processor(s) 132 may be configured to execute one or more additional components that may perform some or all of the functionality attributed below to one of components 108, 110, 114, 118, and/or 120.

Figure 2:
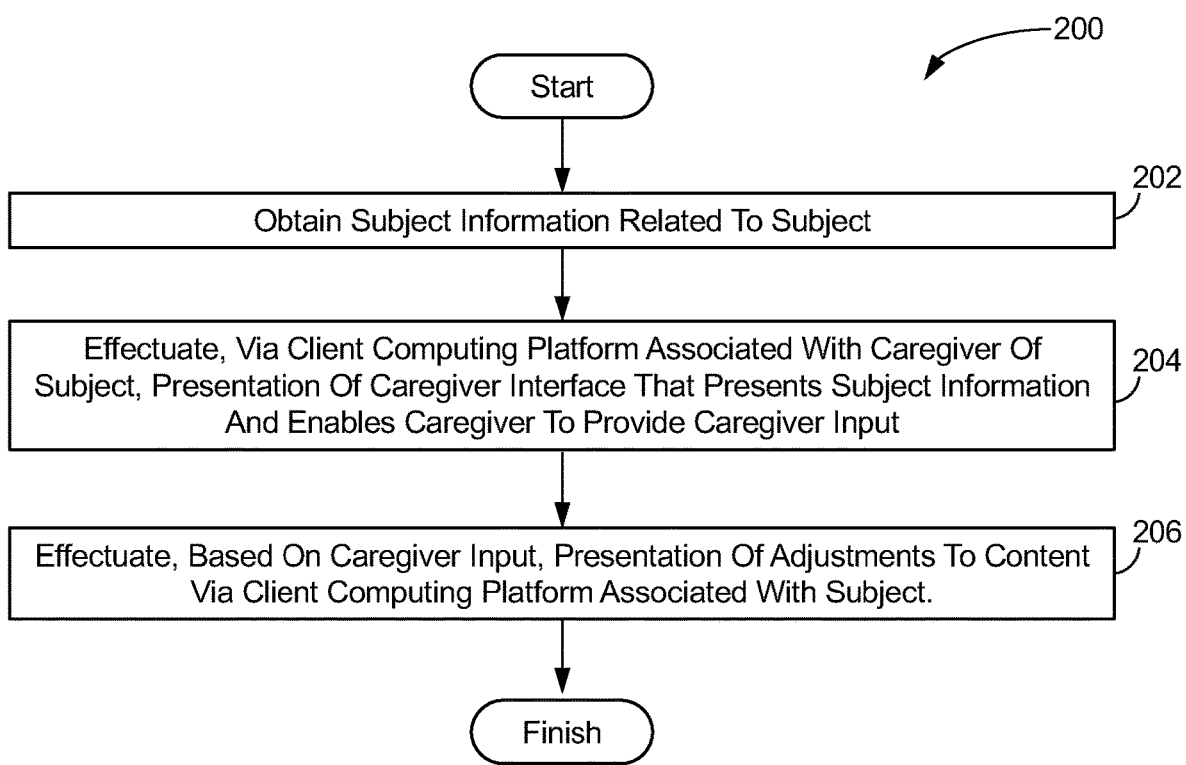
FIG. 2 illustrates a method to facilitate adjusting content to facilitate therapeutic outcomes of subjects, in accordance with one or more implementations.

FIG. 2 illustrates a method 200 to facilitate adjusting content to facilitate therapeutic outcomes of subjects, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining subject information related to subjects. The subject information may characterize (i) physiological health of the subject, (ii) a psychological profile of the subject, and (iii) a therapeutic outcome for the subject to achieve. Operation 202 may be performed by one or more hardware processors configured by machine-readable instructions including a component that is the same as or similar to obtainment component 108, in accordance with one or more implementations.

An operation 204 may include effectuate presentation of a caregiver interface that presents the subject information and enables a caregiver to provide caregiver input. The caregiver interface may be presented via a client computing platform associated with the caregiver of the subject. Operation 204 may be performed by one or more hardware processors configured by machine-readable instructions including a component that is the same as or similar to interface presentation component 110, in accordance with one or more implementations.

An operation 206 may include effectuate presentation of the adjustments to the content via a client computing platform associated with the subject. The adjustments may be presented based on the caregiver input. Operation 206 may be performed by one or more hardware processors configured by machine-readable instructions including a component that is the same as or similar to adjusting component 118, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to facilitate adjusting content to facilitate therapeutic outcomes of subjects, the system comprising:
    one or more processors configured by machine-readable instruction to:
        obtain subject information that characterizes physiological health and psychology of individual subjects and one or more therapeutic outcomes for the individual subjects to achieve;
        effectuate, via a client computing platform associated with a caregiver of the subjects, presentation of a caregiver interface that presents the subject information and enables the caregiver to provide caregiver input for the individual subjects, wherein the caregiver input causes adjustments to (i) content presented to the individual subjects within a virtual environment and (ii) an engagement level of the content, wherein the content facilitates achievement of the therapeutic outcome by the individual subjects;
        effectuate, based on the caregiver input, presentation of the adjustments to the content via client computing platforms associated with the subjects; and
        automatically effectuate presentation of a supplementary adjustment to the engagement level, via the client computing platforms associated with the subjects, based on machine learning, the subject information, and the adjustments caused by the caregiver input.

2. The system of claim 1, wherein the content includes one or more of a recommendation for the subjects, status display and composition, a difficulty level, rewards, and/or an interaction interface, wherein the recommendations include one or more of a to-do list, a quest, educational information, and/or an alliance, wherein the status display and composition includes a metric of achievement, a leaderboard, and/or aesthetics, wherein rewards include badges, streaks, points, and/or virtual items.

3. The system of claim 2, wherein the adjustments to the engagement level gradually adjusts the content between the engagement levels, wherein the engagement levels range between a highly engaging level to a less-engaging routine level, wherein the highly engaging level is time consuming and compelling, wherein the less-engaging routine level is maintainable long-term.

4. The system of claim 2, wherein adjusting the engagement level includes adjusting particular ones of the content presented.

5. The system of claim 1, wherein the one or more processors are further configured by machine-readable instructions to:
    update, based on the caregiver input, the subject information of the subjects, wherein the updates indicate progress towards achievement of the therapeutic outcome.

6. The system of claim 1, wherein the one or more processors are further configured by machine-readable instructions to:
    determine, based on the subject information, an impact value of the engagement level and/or of the content on the achievement of the one or more therapeutic outcomes by the individual subjects, wherein adjusting the engagement level is based on the impact value.

7. The system of claim 1, wherein the therapeutic outcome includes multiple elements for improvement.

8. The system of claim 1, wherein the caregiver input includes milestones to a path to achieve the one or more therapeutic outcomes, wherein the adjustments are based on achievement of one or more milestones.

9. The system of claim 1, wherein the one or more processors are further configured by machine-readable instructions to:
    generate a notification of the supplementary adjustment to the engagement level; and
    effectuate presentation of the notification via the caregiver interface for the caregiver.

10. A method to facilitate adjusting content to facilitate therapeutic outcomes of subjects, the method comprising:
    obtaining subject information that characterizes physiological health and psychology of individual subjects and one or more therapeutic outcomes for the individual subjects to achieve;
    effectuating, via a client computing platform associated with a caregiver of the subjects, presentation of a caregiver interface that presents the subject information and enables the caregiver to provide caregiver input for the individual subjects, wherein the caregiver input causes adjustments to (i) content presented to the individual subjects within a virtual environment and (ii) an engagement level of the content, wherein the content facilitates achievement of the therapeutic outcome by the individual subjects;

effectuating, based on the caregiver input, presentation of the adjustments to the content via client computing platforms associated with the subjects; and automatically effectuating presentation of a supplementary adjustment to the engagement level, via the client computing platforms associated with the subjects, based on machine learning, the subject information, and the adjustments caused by the caregiver input.

11. The method of claim 10, wherein the content includes one or more of a recommendation for the subjects, status display and composition, a difficulty level, rewards, and/or an interaction interface, wherein the recommendations include one or more of a to-do list, a quest, educational information, and/or an alliance, wherein the status display and composition includes a metric of achievement, a leaderboard, and/or aesthetics, wherein rewards include badges, streaks, points, and/or virtual items.

12. The method of claim 11, wherein the adjustments to the engagement level gradually adjusts the content between the engagement levels, wherein the engagement levels range between a highly engaging level to a less-engaging routine level, wherein the highly engaging level is time consuming and compelling, wherein the less-engaging routine level is maintainable long-term.

13. The method of claim 11, wherein adjusting the engagement level includes adjusting particular ones of the content presented.

14. The method of claim 10, further comprising:
updating, based on the caregiver input, the subject information of the subjects, wherein the updates indicate progress towards achievement of the therapeutic outcome.

15. The method of claim 10, further comprising:
determining, based on the subject information, an impact value of the engagement level and/or of the content on the achievement of the one or more therapeutic outcomes by the individual subjects, wherein adjusting the engagement level is based on the impact value.

16. The method of claim 10, wherein the therapeutic outcome includes multiple elements for improvement.

17. The method of claim 10, wherein the caregiver input includes milestones to a path to achieve the one or more therapeutic outcomes, wherein the adjustments are based on achievement of one or more milestones.

18. The method of claim 10, further comprising:
generating a notification of the supplementary adjustment to the engagement level; and
effectuating presentation of the notification via the caregiver interface for the caregiver.

* * * * *